US00PP09565P

United States Patent [19]

Hrebeniuk

[11] Patent Number: Plant 9,565

[45] Date of Patent: May 28, 1996

[54] POINSETTIA PLANT NAMED 'NUTCRACKER PINK'

[75] Inventor: Alexander Hrebeniuk, Sugar Run, Pa.

[73] Assignee: Oglevee, Ltd., Connellsville, Pa.

[21] Appl. No.: 394,377

[22] Filed: Feb. 24, 1995

[51] Int. Cl.[6] ..... A01H 5/00

[52] U.S. Cl. ..... Plt./86.3

[58] Field of Search ..... Plt./86.3

[56] References Cited

U.S. PATENT DOCUMENTS

P.P. 9,177 6/1995 Hrebeniuk ..... Plt./86.4

OTHER PUBLICATIONS

Sigurbjörnsson, B., "Chapter 8, Induced Mutations" *Crop Breeding* 1983 ASA & CSSA, Madison, WI. pp. 153–176.

*Primary Examiner*—James R. Feyrer
*Attorney, Agent, or Firm*—Webb Ziesenheim Bruening Logsdon Orkin & Hanson

[57] ABSTRACT

A poinsettia plant named "Nutcracker Pink" particularly characterized by the combined characteristics of triple form, dark leaves, red non-fading bracts, and particularly its heat resistance. Plants are long lasting in shipment, greenhouse and home, and have upright and compact growth habit with free branching.

1 Drawing Sheet

BACKGROUND OF THE NEW PLANT

The present invention comprises a new and distinct cultivar of *Euphorbia pulcherrima* known by the varietal name "Nutcracker Pink".

The new cultivar was discovered in a planned mutation program of variety H-327 (which is the subject matter of Plant patent application Ser. No. 08/257,102, now U.S. Plant Pat. No. 9,177) in November of 1993 in Sugar Run, Pa. During the mutation program, unrooted cuttings were subjected to 4,000 rads of gamma rays at Penn State Brazelle Nuclear Reactor (cobalt 60, 1.25 MEV) for 2½ minutes. The new cultivar was first asexually reproduced by cuttings in June of 1994 in Sugar Run, Pa. and has been repeatedly asexually reproduced by cuttings at Sugar Run, Pa. Continued observations from the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Pink color of bracts.

2. Ovate shaped bracts having a broad base, more layers which are spaced further apart than commercial varieties and are non-drooping.

3. An above average number of cyathia, which are held tightly together on short stalks and are long lasting.

4. Good branching; uprising; resistance to breakage. The new cultivar differs from its parent essentially only in the bract coloration.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The color readings were determined under cool white light (150 F.C.) at 11:00 a.m. on Dec. 13, 1994 at Connellsville, Pa. Color references are primarily to The R.H.S. Colour Chart of The Royal Horticultural Society of London.

The plant:

*Branching.*—Self branching.

*Rooting.*—Fast.

*Blooming habit.*—8½ week response.

*Response time under black cloth.*—Will take high temperature without fading or loss of blooming.

*Blooming season.*—Blooming occurs in 9 weeks; plant is saleable 6 weeks from initiation.

*Height.*—Up to 18" on a single stem and 10" to 12" on a pinched stem.

Foliage:

*Size.*—Medium.

*Quantity.*—Average, up to 16 leaves per stem.

*Color.*—New foliage — Upper side, Green Group 137 A. Under side, Green Group 138 B. Old foliage — Upper side, Green Group 137 A. Under side, Green Group 138 B. Leaf petiole — Yellow-Green Group 146 C.

*Shape.*—Ovate.

*Texture.*—Veins slightly pronounced; "V" shaped rippled.

*Edge of margin.*—Smooth.

*Aspect.*—Medium green in color and slightly drooped.

*Veins.*—Location — 1 large center midrib; many veins from midrib to edge of leaf. Color — Yellow-Green Group 146 C. Disease resistance — Good resistance to botrytis and mildew.

Flower:

*Borne.*—Prominent on short stalks; held tightly together.

*Quantity.*—Above average, 12–14 cyathia.

*Color.*—Predominately golden yellow with spots of red and green.

Bracts:

*Size.*—Spread is 12" to 16" in diameter; individuals are 3½" to 4½" wide by 5" to 7" long.

*Number of layers.*—Triple.

*Quantity.*—20 to 30 bracts.

*Shape.*—Ovate.

*Color.*—Red Group 54 B (old); Red Group 54 C (young).

*Margin.*—Smooth.

*Veins.*—Location — Pinnate. Color — Red Group 53 C.

Reproductive organs: Typical for poinsettia cultivars.

*Stamens.*—Number — Fifteen. Color — White, turning brown with age.

*Pollen color.*—Yellow.

*Style color.*—Red Group 53 C.

*Ovary color.*—Yellow-Green Group 146 C.

*Nectar cup color.*—Yellow Group 13 C with Red Group 53 C edges.

I claim:

1. A new and distinct variety of poinsettia plant as herein shown and described, particularly characterized by its heat resistance, pink, multi-layered and non-dropping bracts having a broad base, above average number of long lasting cyathia which are held tightly together on short stalks and good branching, uprising and resistance to breakage.

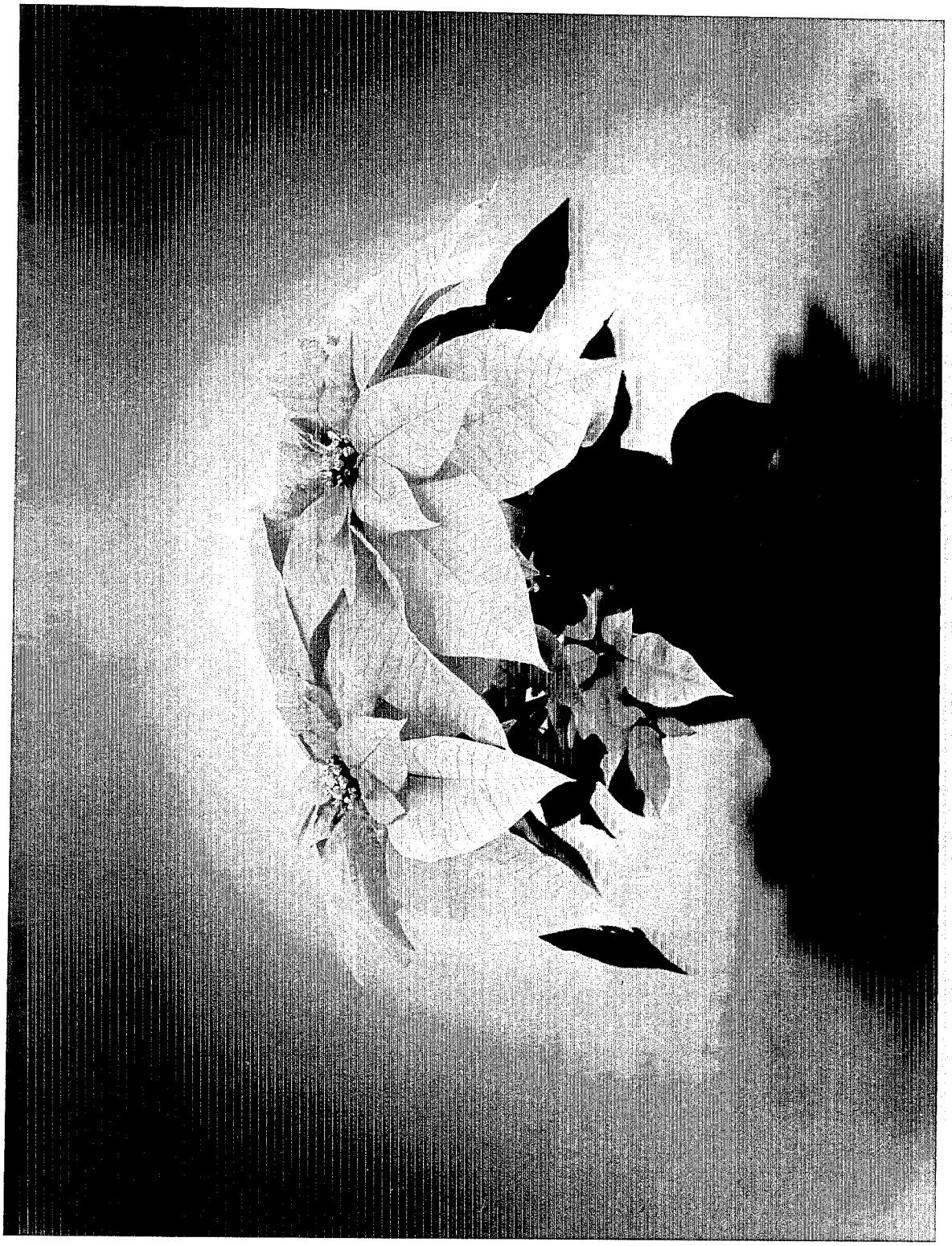

* * * * *